United States Patent [19]

Fukushima et al.

[11] 4,327,086

[45] Apr. 27, 1982

[54] PROCESS FOR HEAT TREATMENT OF AQUEOUS SOLUTION CONTAINING HUMAN BLOOD COAGULATION FACTOR XIII

[75] Inventors: Tsunekazu Fukushima, Kobe; Tomiyuki Matsunaga, Hirakata; Satoshi Funakoshi, Katano, all of Japan

[73] Assignee: The Green Cross Corporation, Osaka, Japan

[21] Appl. No.: 245,971

[22] Filed: Mar. 20, 1981

[30] Foreign Application Priority Data

Mar. 27, 1980 [JP] Japan .................................. 55-40050

[51] Int. Cl.$^3$ ...................... A61K 37/00; A61K 35/14; A61K 35/48
[52] U.S. Cl. .................................... 424/177; 424/101; 424/105
[58] Field of Search ........................ 424/101, 177, 105

[56] References Cited

PUBLICATIONS

Chem. Abst. 9th Collect Index Chem. Subst. Index 1972–1976, p. 7801.

*Primary Examiner*—Sam Rosen
*Attorney, Agent, or Firm*—Cushman, Darby & Cushman

[57] ABSTRACT

A process for heat treatment to inactive hepatitis virus in human blood coagulation factor XIII compositions, which is characterized in that the heat treatment at 50° to 80° C. of an aqueous solution containing the human blood coagulation factor XIII is carried out for 3 to 15 hours in the presence of 10% (W/V) or more of at least one principal stabilizer selected from the group consisting of neutral amino acids, monosaccharides and sugar alcohols and 10% (W/V) or more of at least one auxiliary stabilizer selected from the group consisting of salts of organic carboxylic acids having 3 to 10 carbon atoms.

9 Claims, No Drawings

PROCESS FOR HEAT TREATMENT OF AQUEOUS SOLUTION CONTAINING HUMAN BLOOD COAGULATION FACTOR XIII

This invention relates to a process of heat treatment to inactivate the hepatitis virus in an aqueous solution containing the human blood coagulation factor XIII.

The blood coagulation factor XIII (hereinafter referred to briefly as factor XIII) participates in the formation of a stable fibrin polymer in the final stage of blood coagulation mechanism, and is also called fibrin stabilizing factor. Under normal conditions it exists in an inactive form in the blood. However, in the event of formation of thrombin upon coagulation of blood after hemorrhage or the like, the factor XIII becomes activated by the action of thrombin and calcium ion and strives for the stabilization of fibrin. Therefore, in a blood suffering from diminution or deficiency of the factor XIII, although the coagulation time shows a normal threshold, the formed fibrin clot is fragile, giving rise to characteristic phenomena such as secondary hemorrhage and the like.

The clinical applications of the factor XIII preparations include not only treatment for disorders due to congenital or acquired deficiency or diminution in factor XIII but also promotion of wound healing after surgical operations in a broad range.

In recent years, however, the onset of serum hepatitis accompanied with transfusion has become one of the serious social problems and the cause was found to be attributable to the hepatitis virus. The individual preparation of serum proteins separated by the fractionation of blood plasma also involves the problem of onset of hepatitis.

The factor XIII, which is the subject of this invention, is also one of the human serum protein preparations and is likewise apprehensive of the contamination with hepatitis virus.

In order to solve the problem of hepatitis infection, it was found that the infective activity of hepatitis virus in serum protein preparations in general, particularly in albumin preparations, may be controlled by the heat treatment at 60° for 10 hours without causing the denaturation of albumin. Since the albumin preparation subjected to such a heat treatment has been clinically used with safety, the method of inactivating the hepatitis virus by the heat treatment at 60° C. for 10 hours is now being adapted to other human serum protein preparations. However, in order to apply such a heat treatment, the substance being treated must be stable to the treatment.

When the factor XIII was heated in an aqueous solution at 60° C. for 10 hours, its activity was found to be markedly deteriorated. The present inventors previously succeeded in markedly improving the stability of an aqueous solution containing the factor XIII against the heat treatment at 60° C. for 10 hours by adding a neutral amino acid, a sugar alcohol and a monosaccharide each in a concentration of 10% or more, thus making possible the inactivation treatment of hepatitis virus in a medicinal preparation [Japanese Patent Application "Kokai" (Laid-open) No. 59,018/1978].

The present inventors subsequently found that in the above method of heat stabilization, the heat stability of factor XIII could be further improved by the supplementary addition of a specific organic carboxylic acid salt. The present invention has been accomplished on the basis of said finding.

An object of this invention is to provide a novel heat treatment process in which the inactivation treatment of hepatitis virus in an aqueous solution containing the human blood coagulation factor XIII is carried out under those conditions which increase the thermal stability of said factor.

Other objects and advantages of this invention will become apparent from the following description.

According to this invention there is provided a process for heat treatment, characterized in that the heat treatment at 50° to 80° C. of an aqueous solution containing the human blood coagulation factor XIII is carried out for 3 to 15 hours in the presence of 10 to 30% (W/V) of a principal stabilizer selected from the group consisting of neutral amino acids, monosaccharides and sugar alcohols and 10 to 30% (W/V) of an auxiliary stabilizer selected from the group consisting of salts of organic carboxylic acids having 3 to 10 carbon atoms.

The factor XIII being heat treated is subject to no particular limitation, so far as it is originated from man. It is contained in blood plasma, platelet and placenta in comparatively large quantities and methods for its recovery from respective materials have been known [Loewy, A. G., Journal of Biological Chemistry, 236, 2625 (1961); Januszko, B. T., Nature, 191, 1093 (1961); Bohn, V. H., Blut, 25, 235 (1972)]. Of these materials, because of their high prices, blood plasma and platelet are unsuitable for the large-scale production of factor XIII. As contrasted, the placenta contains a comparatively large quantity of factor XIII and is easily available. Therefore, the recovery from the placenta is most attracting the attention at present.

Preparation of the factor XIII from the placenta can be carried out by several methods such as a method for purifying the factor XIII by a combined precedure involving gel filtration and fractionations using ammonium sulfate, 2-ethoxy-6,9-diaminoacridine lactate (acrinol) and alcohol [Blut, 25, 235 (1972)]; a method utilizing principally the ammonium sulfate fractionation technique (Japanese Patent Application "Kokai" (Laid-open) No. 59,018/1978), and a fractionation method employing an alkylene oxide polymer (Japanese Patent Application "Kokai" (Laid-open) No. 64,522/1980, European Patent Application No. 79104346.6). Although the degree of purification of factor XIII is not specifically restricted, it is desirable to use an aqueous solution of factor XIII having an activity of 5 to 500 units/ml, as assayed by the method described in Thrombosis, Diathesis Haemorrhagica, 23, 455 (1970). The factor XIII content of the aqueous solution to be heat-treated is preferably 0.1 to 10% (W/V) in terms of protein and the pH of the solution is generally 5 to 10, preferably 6.5 to 8.5 and adjusted most preferably with a suitable buffer solution of a low salt concentration.

The neutral amino acids, monosaccharides and sugar alcohols for use as principal stabilizers are described in detail in Japanese Patent Application "Kokai" (Laid-open) No. 59,018/1978. Nonlimitative examples include neutral amino acids such as glycine and alanine, monosaccharides such as glucose, xylose, and fructose, and sugar alcohols such as mannitol, galactitol, glucosaminitol, sorbitol, and galactosaminitol. There may be used each alone or in combinations. The amount to be added of principal stabilizers is generally 10% (W/V) or more, preferably 10 to 30% (W/V) in practice. If present in an amount less than 10% (W/V), the principal stabilizers will exhibit only unsatisfactory stabilizing effect.

The organic carboxylic acid having 3 to 10 carbon atoms used in the form of a salt as the auxiliary stabilizer according to this invention is a hydrocarbon moiety combined with a carboxyl group. The hydrocarbon moiety may be saturated or unsaturated. Examples of such hydrocarbon moieties include alkyl groups, aryl groups (e.g. phenyl group) and aralkyl groups. The number of carboxyl group may be singular or plural, preferably one or two. The carboxylic acid may contain a hydroxyl group as substituent. Although the salt of said organic carboxylic acid to be used in the present process may be any so far as it is physiologically acceptable, alkali metal salts (e.g. sodium salt and potassium salt) and alkaline earth metal salts (e.g. calcium salt) are preferred and sodium salt and potassium salt are most preferred.

Examples of suitable organic carboxylic acid salts include physiologically acceptable salts, preferably alkali metal salts (sodium salts and potassium salts) of propanoic acid, butanoic acid, pentanoic acid, caprylic acid, caproic acid, malonic acid, succinic acid, glutaric acid, adipic acid, citric acid and mandelic acid. These salts are used each alone or in combinations. The amount to be added of an organic carboxylic acid salt is 10% (W/V) or more, preferably 10 to 30% (W/V) in practice. If the amount is below 10% (W/V), the effectiveness as an auxiliary stabilizer will be unsatisfactory.

The temperature of heat treatment is 50° to 80° C., preferably 60° C. and the time of heating is 3 to 15 hours, preferably 10 hours.

After the heat treatment according to this invention, the aqueous solution containing the factor XIII shows an electric conductivity two to five times as high as that of untreated solution. Consequently, before purification, the heat-treated aqueous solution is dialyzed, diluted, or centrifuged to separate the factor XIII as a precipitate. Then the purification may be performed in known ways. If the recovered factor XIII has a sufficiently high purity, it is made into medicinal preparations by customary pharmaceutical procedures such as sterile filtration, dispensation and lyophilization.

In the case of crude factor XIII, it is purified by a combination of known purification procedures for factor XIII, such as chromatography with an anion exchanger, treatment with a molecular sieve, and fractionation by use of PEG, acrinol or the like.

In order to examine the effectiveness of the heat treatment of this invention, a preparation of human factor XIII which has been recovered from a HBsAg (hepatitis virus antigen)-positive blood plasma was heat-treated at 60° C. for 10 hours under the conditions as herein specified. A portion of the preparation corresponding to a factor XIII activity of 500 units (as assayed by the method previously described) was inoculated into a chimpanzee to observe the onset of hepatitis. After one month, no sign of hepatitis was observed.

As described above, the heat treatment process of this invention is capable of perfectly inactivating the infectivity of hepatitis virus which is liable to contaminate the factor XIII preparation, a precious blood preparation, thereby causing no loss in factor XIII activity. The heat treatment according to this invention, therefore, has a remarkable advantage in the commercial production of factor XIII preparations involving a virus inactivation step.

The invention is illustrated below with reference to Example but the invention is not limited thereto.

EXAMPLE

To one liter of an aqueous solution containing 100 units (activity)/ml of factor XIII dissolved in a 0.05 M phosphate buffer solution (pH 7.0), were added 150 g of glycine and 150 g of trisodium citrate. After thorough stirring, the mixture was heated at 60° C. for 10 hours. After cooling, the mixture was centrifuged to separate a precipitate which was again dissolved in the 0.05 M phosphate buffer solution (pH 7.0). The resulting solution was dialyzed against a 0.5 M phosphate buffer solution (pH 7.2) containing 0.005 M EDTA to obtain a clear solution. To this solution was added 500 g (wet weight) of QAE.Sephadex, which had been equilibrated with the same buffer solution as used above, to adsorb thereon the factor XIII. The effluent fractions obtained by elution with a 0.5 M sodium chloride solution were combined and dialyzed against a 0.5% sodium chloride solution containing 2.25% of glycine. The dialyzed solution was sterile-filtered, dispensed and lyophilized.

EXPERIMENTAL EXAMPLE

A series of experiments were conducted to evaluate the stabilizing effect of various additives on the heat treatment. In the experiment one liter of an aqueous solution containing 500 units (activity)/ml of factor XIII was used. After addition of various additives in varied amounts as shown in Table 1, the solution was treated at 60° C. for 10 hours. The retention (%) of total activity based on the activity of untreated solution in each case was as shown in Table 1. From the results it is seen that each principal stabilizer exhibits an increased stabilizing effect in the presence of an auxiliary stabilizer.

TABLE 1

| Principal stabilizer | % (W/V) | Auxiliary stabilizer | % (W/V) | Retention of activity (%) |
|---|---|---|---|---|
| Glycine | 15 | Trisodium citrate | 0 | 50 |
| | | | 10 | 85 |
| | | | 15 | 90 |
| | | | 20 | 90 |
| | 25 | Sodium caprylate | 0 | 50 |
| | | | 10 | 86 |
| | | | 15 | 92 |
| | | | 20 | 92 |
| Alanine | 25 | Sodium citrate | 0 | 25 |
| | | | 10 | 65 |
| | | | 20 | 69 |
| Mannitol | 15 | Sodium mandelate | 0 | 50 |
| | | | 10 | 81 |
| | | | 15 | 91 |
| | | | 20 | 90 |
| | 25 | Sodium caproate | 0 | 50 |
| | | | 10 | 82 |
| | | | 15 | 90 |
| | | | 20 | 91 |
| | 15 | Sodium caprylate | 0 | 50 |
| | | | 10 | 89 |
| | | | 15 | 91 |
| | | | 20 | 90 |
| | 25 | Sodium caprylate | 0 | 50 |
| | | | 10 | 85 |
| | | | 15 | 92 |
| | | | 20 | 93 |
| Glucose | 15 | Disodium glutarate | 0 | 25 |
| | | | 10 | 69 |
| | | | 15 | 71 |
| | | | 20 | 73 |
| | 25 | Disodium malonate | 0 | 25 |
| | | | 10 | 71 |
| | | | 15 | 73 |

TABLE 1-continued

| Principal stabilizer | % (W/V) | Auxiliary stabilizer | % (W/V) | Retention of activity (%) |
|---|---|---|---|---|
| | | | 20 | 75 |
| None | | None | | 0 |

What is claimed is:

1. A process for heat treatment to inactive hepatitis virus in human blood coagulation factor XIII compositions, which comprises carrying out the heat treatment at 50° to 80° C. of an aqueous solution containing the human blood coagulation factor XIII for 3 to 15 hours in the presence of 10% (W/V) or more of at least one principal stabilizer selected from the group consisting of neutral amino acids, monosaccharides and sugar alcohols and 10% (W/V) or more of at least one auxiliary stabilizer selected from the group consisting of salts of organic hydrocarbon and hydroxyhydrocarbon carboxylic acids having 3 to 10 carbon atoms.

2. A process according to claim 1, wherein the salts of organic carboxylic acids are physiologically acceptable salts of propanoic acid, butanoic acid, pentanoic acid, caprylic acid, caproic acid, malonic acid, succinic acid, glutaric acid, adipic acids, citric acid and mandelic acid.

3. A process according to claim 2, wherein the physiologically acceptable salt is a sodium or a potassium salt.

4. A process according to claim 1, wherein the neutral amino acid is present and is glycine or alanine.

5. A process according to claim 1, wherein the monosaccharide is present and is glucose, xylose or fructose.

6. A process according to claim 1, wherein the sugar alcohol is present and is mannitol, galactitol, glucosaminitol, sorbitol or galactosaminitol.

7. A process according to claim 1, wherein the principal stabilizer and the auxiliary stabilizer are present in amounts of 10 to 30% (W/V) and 10 to 30% (W/V), respectively.

8. A process according to claim 1 wherein the auxiliary stabilizer is a salt of an organic hydrocarbon carboxylic acid having 3 to 10 carbon atoms.

9. A process according to claim 1 wherein the auxiliary stabilizer is a salt of an organic hydroxyhydrocarbon carboxylic acid having 3 to 10 carbon atoms.

* * * * *